United States Patent
Zijp et al.

(10) Patent No.: US 7,349,564 B2
(45) Date of Patent: Mar. 25, 2008

(54) IMAGING INTERNAL STRUCTURES

(75) Inventors: Lambert Zijp, Amsterdam (NL); Kevin John Brown, Crawley (GB); David Jaffray, Etobicoke (CA); Jeffrey H. Siewerdsen, Toronto (CA); Marcel van Herk, Amsterdam (NL); Jan-Jakob Sonke, Amsterdam (NL)

(73) Assignee: Elekta AB (PUBL), Stockholm (SE)

( * ) Notice: Subject to any disclaimer, the term of this patent is extended or adjusted under 35 U.S.C. 154(b) by 678 days.

(21) Appl. No.: 10/760,628

(22) Filed: Jan. 20, 2004

(65) Prior Publication Data

US 2004/0234115 A1    Nov. 25, 2004

(30) Foreign Application Priority Data

Jan. 21, 2003 (GB) .................................. 0301278.8
Nov. 28, 2003 (GB) .................................. 0327675.5

(51) Int. Cl.
*G06K 9/00* (2006.01)
(52) U.S. Cl. ...................................................... 382/131
(58) Field of Classification Search ................ 382/131; 387/4

See application file for complete search history.

(56) References Cited

U.S. PATENT DOCUMENTS

| | | | |
|---|---|---|---|
| 1,576,588 A | | 3/1978 | Richey et al. |
| 4,858,128 A * | | 8/1989 | Nowak .......................... 382/131 |
| 5,231,443 A * | | 7/1993 | Subbarao ....................... 396/93 |
| 5,835,880 A * | | 11/1998 | Gan et al. ...................... 701/205 |
| 6,005,983 A * | | 12/1999 | Anderson et al. .............. 382/254 |
| 6,278,530 B1 * | | 8/2001 | Ulichney et al. ............... 358/3.13 |
| 6,366,688 B1 * | | 4/2002 | Jun et al. ........................ 382/145 |
| 6,381,375 B1 * | | 4/2002 | Reyzin ............................ 382/276 |
| 6,434,215 B1 * | | 8/2002 | Cesmeli ............................ 378/8 |

(Continued)

FOREIGN PATENT DOCUMENTS

GB    2250164 A    5/1992

(Continued)

OTHER PUBLICATIONS

Kacheiriess, M., et al, "Electrocardiogram-correlated image reconstruction from subsecond spiral computed tomography scans of the heart", *Medical Physics*, pp. 2416-2431, Dec. 1998, vol. 25, No. 12.

*Primary Examiner*—Jingge Wu
*Assistant Examiner*—Max Shikhman
(74) *Attorney, Agent, or Firm*—Bromberg & Sunstein LLP

(57) ABSTRACT

An apparatus, method and software module for selecting phase-correlated images from the output of a scanner such as a cone beam CT scanner operates by collapsing the images derived from the series from two dimensions to one dimension by summing the intensities of pixels along a dimension transverse to the one dimension, producing a further image from a composite of the one-dimensional images obtained from images in the series, analysing the further image for periodic patterns, and selecting from the series images having like phase in that periodic pattern. If desired, a plurality of reconstructions can be derived at different phases. The analysis of the further image for periodic patterns can include comparing the one-dimensional images therein, to identify a movement of features in that dimension. This allows (inter alia) the accurate determination of the breathing cycle in a patient and a concomitant improvement in the quality of CT scans by using phase-correlated images.

28 Claims, 13 Drawing Sheets

U.S. PATENT DOCUMENTS

| | | |
|---|---|---|
| 6,454,713 B1 | 9/2002 | Ishibashi et al. ............ 600/439 |
| 6,522,712 B1* | 2/2003 | Yavuz et al. .................... 378/4 |
| 6,539,074 B1* | 3/2003 | Yavuz et al. .................... 378/4 |
| 6,560,480 B1* | 5/2003 | Nachaliel et al. ........... 600/547 |
| 6,771,811 B1* | 8/2004 | Walmsley et al. .......... 382/162 |
| 6,937,696 B1* | 8/2005 | Mostafavi .................... 378/95 |
| 2002/0001759 A1* | 1/2002 | Ohashi et al. ................. 430/5 |
| 2003/0182246 A1* | 9/2003 | Johnson et al. ............... 705/76 |
| 2003/0215136 A1* | 11/2003 | Chao et al. ................. 382/176 |
| 2004/0066977 A1* | 4/2004 | Bickford et al. ............ 382/248 |

FOREIGN PATENT DOCUMENTS

| | | |
|---|---|---|
| JP | 2000201922 | 1/1999 |
| WO | WO 01/95615 | 12/2001 |
| WO | PCT/GB2004/000155 | 1/2004 |

\* cited by examiner

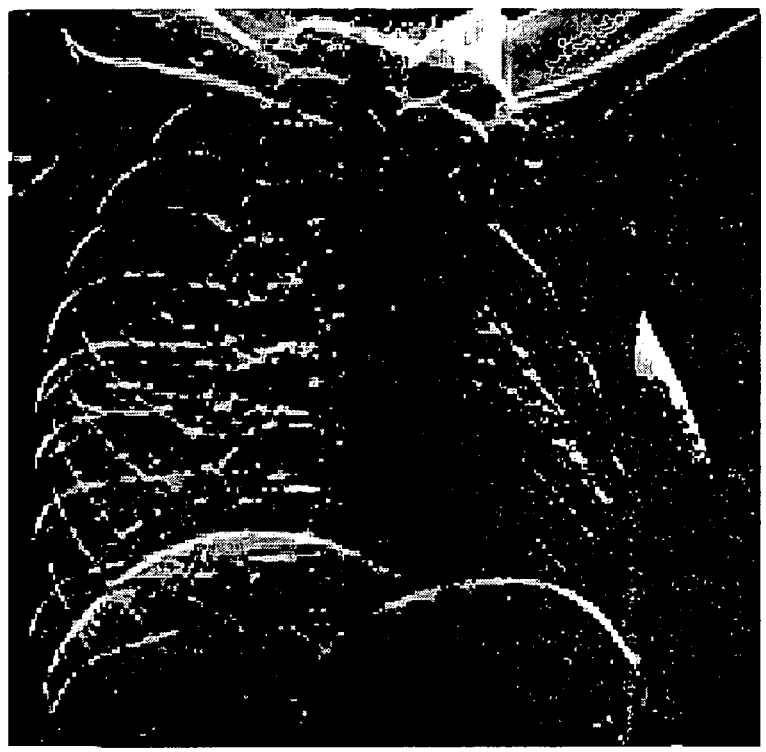
Fig 15     Fig 16
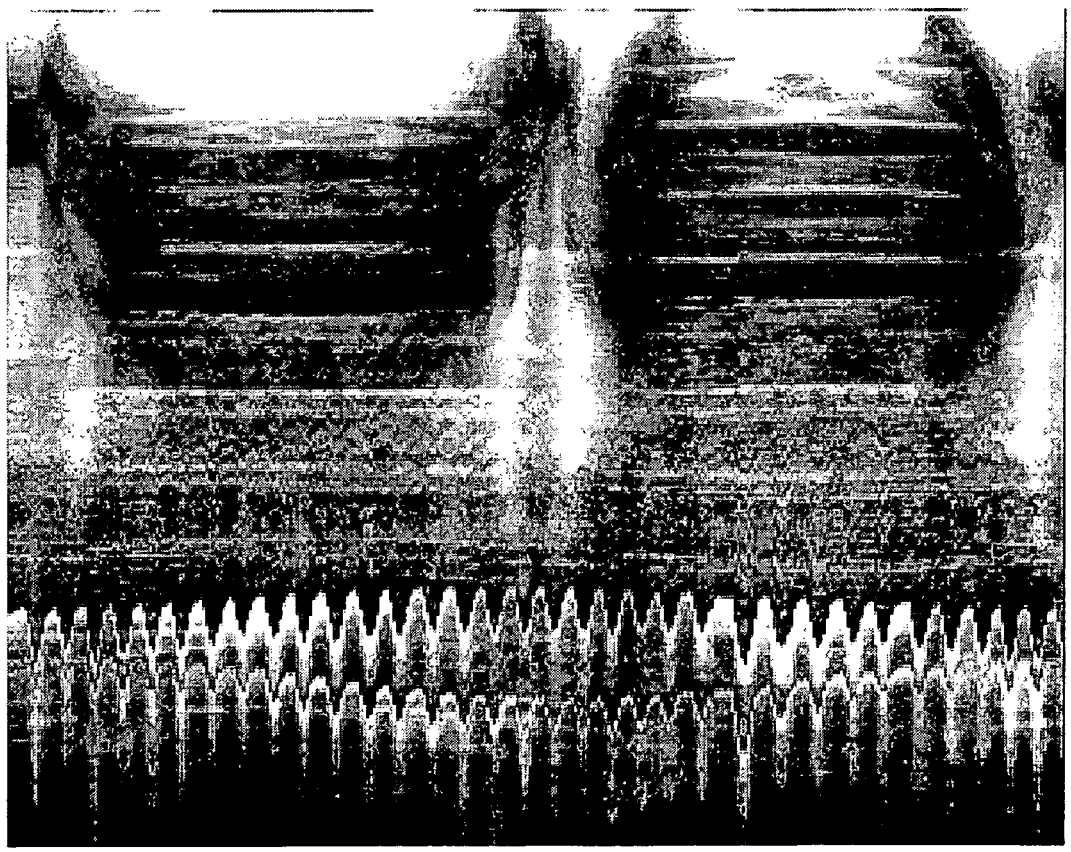
Fig 17

IMAGING INTERNAL STRUCTURES

FIELD OF THE INVENTION

The present invention relates to the imaging of internal structures of a volume. It is particularly (but not exclusively) relevant to the analysis of CT images to eliminate artefacts and inaccuracies caused by a patient's breathing cycle.

BACKGROUND ART

Existing computed tomography (CT) scanners rely on a radiation source and a detector that rotate around the patient and observe the attenuation of the beam as it passes through the patient from a variety of directions. From this data, a three dimensional representation of the internal structure of the patient is computed.

These fall into two distinct groups. First, the simple CT scanner directs a narrow "pencil" beam through the patient. Each complete rotation results in a two dimensional image in the form of a "slice" or section through the patient. The scanner (or the patient) is then indexed along the axis of rotation and a further slice is scanned. These slices can then be assembled into a three dimensional image.

Second, a cone beam CT scanner directs a divergent beam toward the patient to produce (at any selected time) a two dimensional projection of the entire region of interest. As the beam rotates, projections are acquired from different directions and a three-dimensional image can be constructed.

Cone beam CT is in general advantageous as compared to simple CT since its resolution is the same in all directions. Simple CT has a high resolution in the plane of each slice, but the resolution perpendicular to this is limited by the index distance.

Both techniques assume that the patient is static. This is an invalid assumption for a living patient, as some parts such as the heart, lungs and diaphragm will inevitably be moving. As the patient breathes, structures around the lungs and diaphragm will move and this presents difficulties in obtaining good quality scans. In simple CT, artefacts in the image arise; as the slice is indexed along the patient, the breathing cycle can move structures into and out of the slice being scanned at that time. Periodic artefacts thus develop in the reconstructed volume. In cone beam CT, some artefacts result from the reconstruction process, but the main problem is a blurring of the image in the form of an averaging process.

In the treatment of lung tumours (for example) it is important to know the position of the tumour and its movement as the breathing cycle progresses. The time-averaged information derived from cone beam CT is inadequate, as this cannot distinguish between a small tumour that dwells in one area and a large tumour that briefly passes an area.

Hitherto, when performing CT scans of the thorax, patients have been asked to control their breathing in accordance with an external stimulus, or a proxy for the phase of the breathing cycle has been detected. Examples of proxies that have been used include the local temperature around the nostril, and the dimensions of the thorax. These have proved to be of assistance but generally unsatisfactory.

SUMMARY OF THE INVENTION

The accurate determination of a patient's breathing cycle is thus an important diagnostic and treatment-planning tool for a wide range of purposes.

The present invention therefore provides an apparatus for imaging the internal structure of a volume exhibiting an internal variation, comprising a source of penetrating radiation and a two dimensional detector for that radiation, the source and the detector being arranged to produce a series of projected images of the volume, a reconstruction means for deriving information as to the three dimensional structure in the volume from selected images of the series, a selection means for selecting images with similar phase from the series for use by the reconstruction means, wherein the selection means is arranged to collapse the images derived from the series from two dimensions to one dimension by summing the intensities of pixels along a dimension transverse to the one dimension, produce a further image from a composite of the one-dimensional images obtained from images in the series, analyse the further image for patterns, and select from the series images having like phase in that pattern.

It is envisaged that the image handling will be carried out by a computing means, in the form of either a general-purpose computing means equipped with a suitable program or a dedicated computing means designed specifically for this task. In this case, the images referred to will typically be in a digitised form in which numerical values stored in one or more files correspond to intensities or other image features at specific locations in the image.

Thus, when we refer to image manipulation steps, we do not intend to infer that the images must be physically manipulated in this way, but intend to include processes in which numerical values or arrays thereof are manipulated by arithmetic operations or the like. Likewise, the computing means need not physically display, render or otherwise produce the interim images such as the further image referred to above, provided that the arithmetic or other processes are carried out to obtain the corresponding numerical data.

An improved accuracy can be obtained if the images are pre-processed prior to operation of the selection means. This pre-processing preferably includes a number of steps such as filters for narrowing the range of intensities in the image and derivative filters to highlight edges in the image. Where the volume contains a patient, the derivative is preferably carried out in the direction of the craniocordal axis of the patient, as the diaphragm has an edge perpendicular to that direction.

The pre-processing can includes masks applied to the image, such as to select areas including edges and to exclude areas outside the region of interest. A useful mask is one that excludes areas of the image that are external to an object (e.g. a patient) within the volume. An edge mask can be derived from a threshold applied to the image as filtered via a derivative filter.

If desired, a plurality of reconstructions can be derived from a plurality of subsets each containing phase-correlated images from the series, the phase correlation of each subset differing from the phase correlation of other subsets.

The analysis of the further image for periodic patterns preferably includes a step of comparison of the one-dimensional images therein, to identify a movement of features in that dimension. It is preferable to compare adjacent images as these will be the most generally similar and thus differences between them are more likely to be significant. The one-dimensional images can be compared by calculating the difference in intensity between the images at different relative shifts of the images. The rms difference is usually the best measure of difference.

The further image can also be advantageously subjected to processing, prior to analysis for periodic patterns. Suitable pre-processing includes derivative filters to highlight edges in the further image, preferably carried out in a direction transverse to the one dimension, and/or the selection of regions of interest. It is particularly preferred to use the derivative-filtered image to highlight areas with sharp changes and thereby to select a part of the original further image.

The source and detector can be rotateable relative to the volume, such that the series of projected images show the volume in different orientations.

The invention is particularly suited to periodic variations, but is in fact applicable to any variation in the volume.

In general, the invention finds most useful application where the periodic variation is a natural variation exhibited by living organism, such as the breathing cycle. However, it is of general application and need not be limited in this way.

The present invention also provides a method of selecting phase correlated images from the output of a scanner, comprising the steps of, for each of a plurality of images in a series thereof produced by the scanner, collapsing the images from two dimensions to one dimension by summing the intensities of pixels along a dimension transverse to the one dimension, producing a further image from a composite of the one-dimensional images obtained from images in the series, analysing the further image for periodic patterns, and selecting from the series images having like phase in that periodic pattern.

The present invention further provides a software module for selecting phase correlated images from the output of a scanner, arranged to execute the steps of, for each of a plurality of images in a series thereof produced by the scanner, collapsing the images from two dimensions to one dimension by summing the intensities of pixels along a dimension transverse to the one dimension, producing a further image from a composite of the one-dimensional images obtained from images in the series, analysing the further image for periodic patterns, and selecting from the series images having like phase in that periodic pattern.

These additional aspects of the invention are presently best suited to a cone beam CT scanner, especially one in which the images are of a breathing patient.

It should be emphasised that this invention is of potentially wide application to the analysis of the internal arrangement of varying structures, and is not limited to the detection of breathing phase. Other variations in living and non-living structures could be detected, and the invention could be applied to other scanners than cone beam CT scanners. This arises from the nature of the invention in that it does not attempt to identify specifically breathing-related structures (such as the diaphragm) as such but instead merely seeks variations via a novel processing route.

As a result, the invention does in fact identify the diaphragm, when applied to the problem of identifying breathing phase, but does not do so by directly seeking objects of that shape. Indeed, the inventors have found that to do so is counterproductive in that the projected image of the diaphragm changes shape as the scanner rotates around the patient.

BRIEF DESCRIPTION OF THE DRAWINGS

An embodiment of the present invention will now be described by way of example, with reference to the accompanying figures in which;

FIGS. 15 and 16 show the reduction of the image to one dimension;

FIG. 17 shows the further image;

DETAILED DESCRIPTION OF THE EMBODIMENTS

Figure 1:
FIG. 1 shows a typical image of a human thorax as obtained by a simple CT scanner without respiration correlation.
Figure 2:
FIG. 2 shows a typical image of a human thorax as obtained by a cone beam CT scanner without respiration correlation.
Figure 3:
FIG. 3 shows one image of a human thorax from the series thereof as obtained from a cone beam CT scanner.
Figure 4:
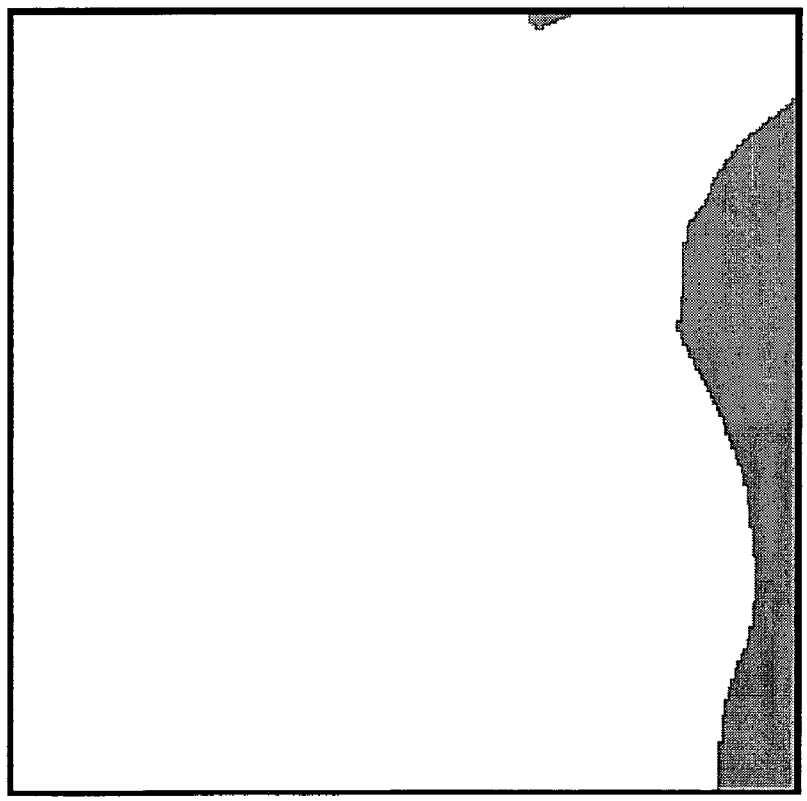
FIG. 4 shows the patient mask derived from the image of FIG. 3.
Figure 5:
FIGS. 5 and 6 show the image of FIG. 3 before and after equalisation.
Figure 6:
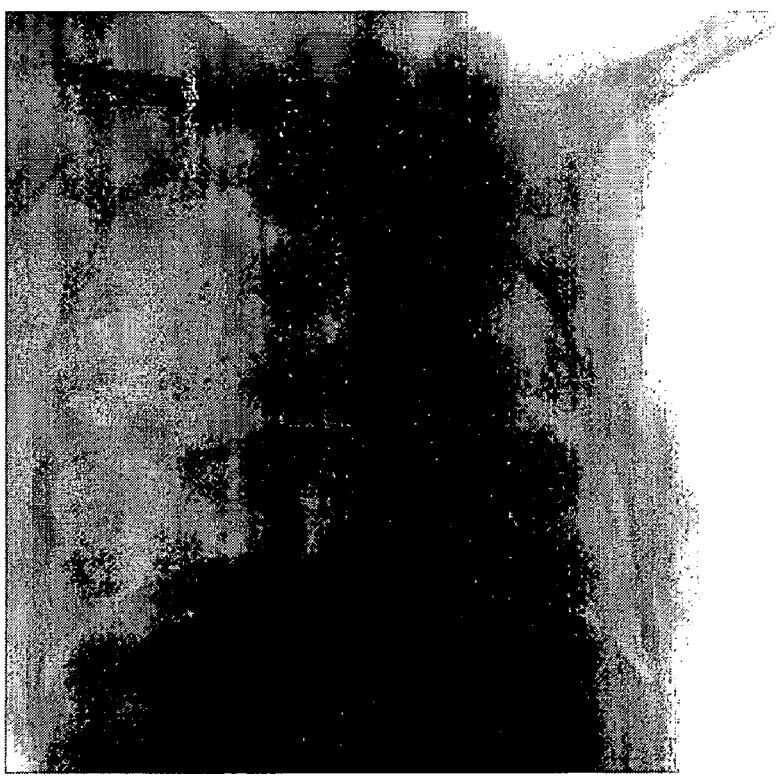
Figure 7:
FIGS. 7 and 8 show the image of FIG. 3 before and after filtering to highlight edges.
Figure 8:
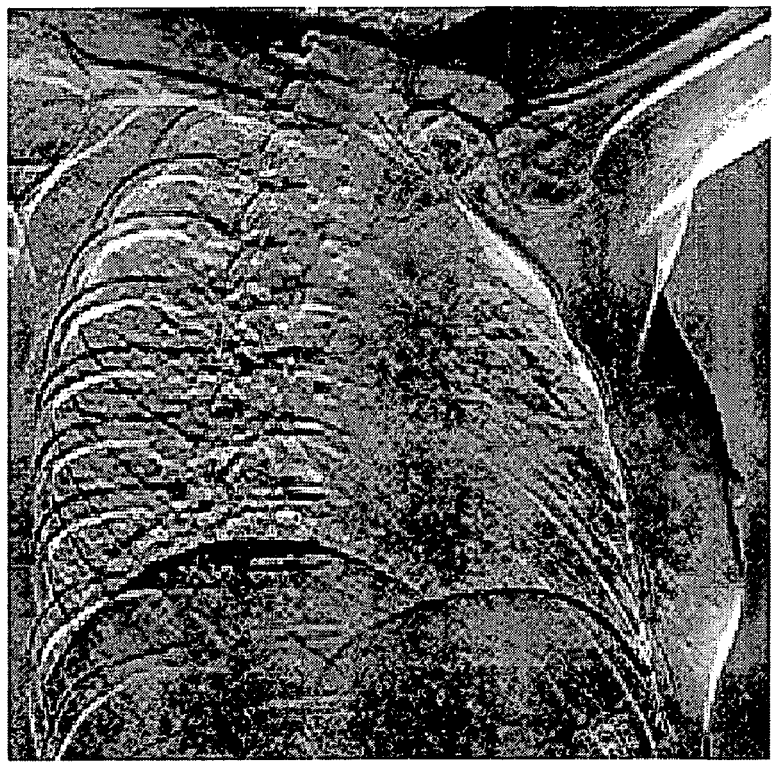
Figure 9:
FIGS. 9 and 10 shows the preparation of an edge mask.
Figure 10:
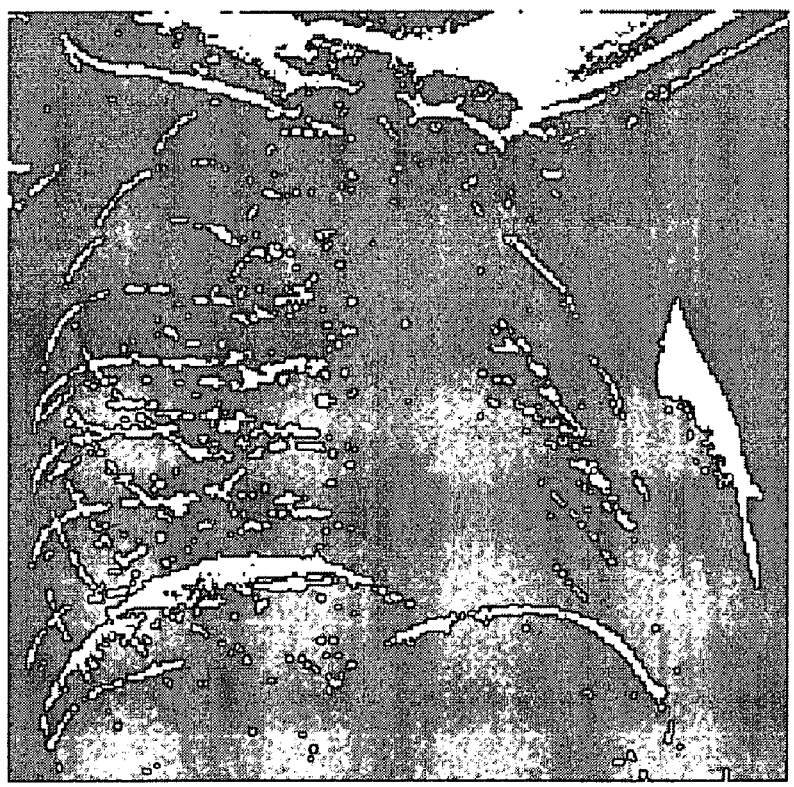
Figure 11:
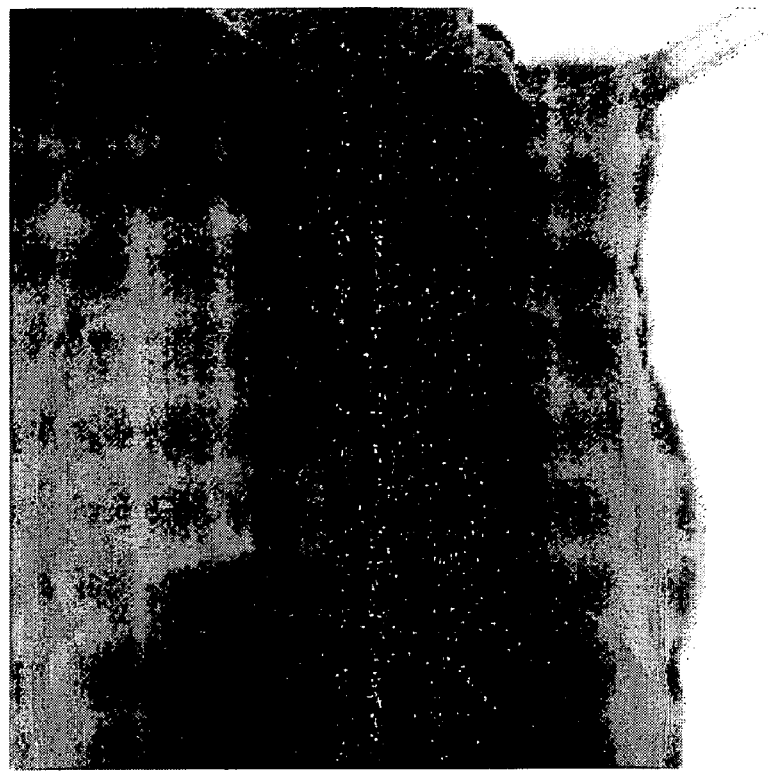
FIGS. 11 and 12 show the application of a gradient norm filter.
Figure 12:
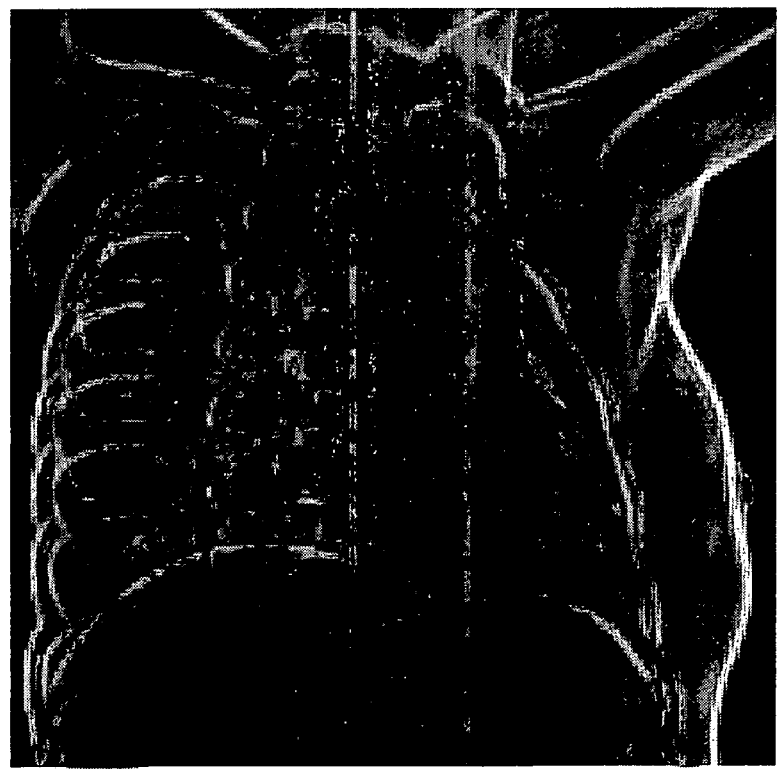
Figure 13:
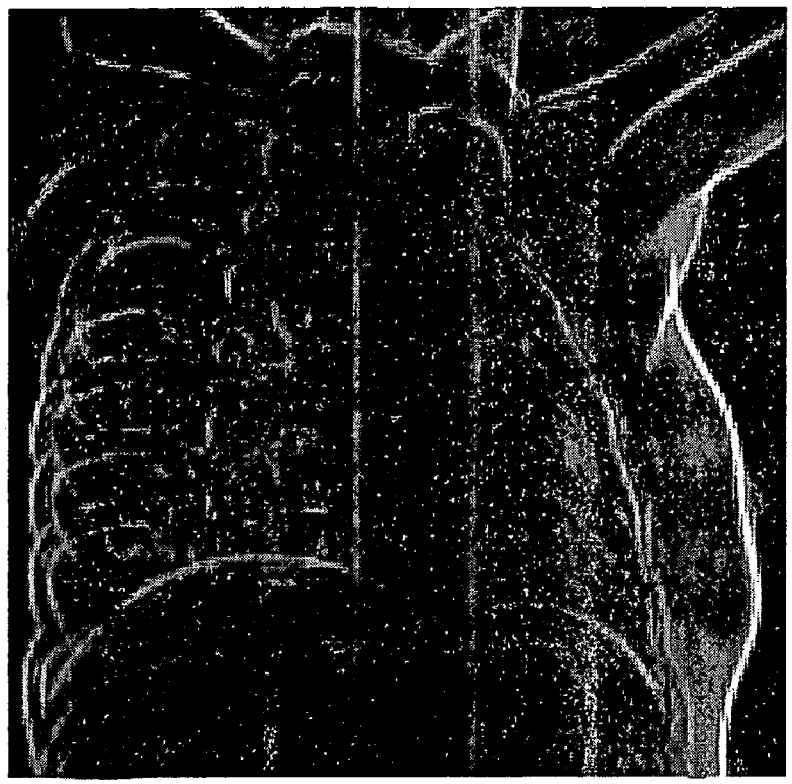
FIGS. 13 and 14 shows the result of applying the patient mask and the edge mask.
Figure 14:

FIG. 1 shows a conventional CT scan of the thorax region of the patient. Periodic artefacts can be seen at (for example) 100, 102 and 104, and correspond to errors caused by interaction of the breathing process with the CT scanning process. Likewise, FIG. 2 shows a typical cone beam CT image of the thorax by a patient, and the areas 106, 108 show significant blurring arising from the internal motion of the patient's lungs and diaphragm.

Figure 22:
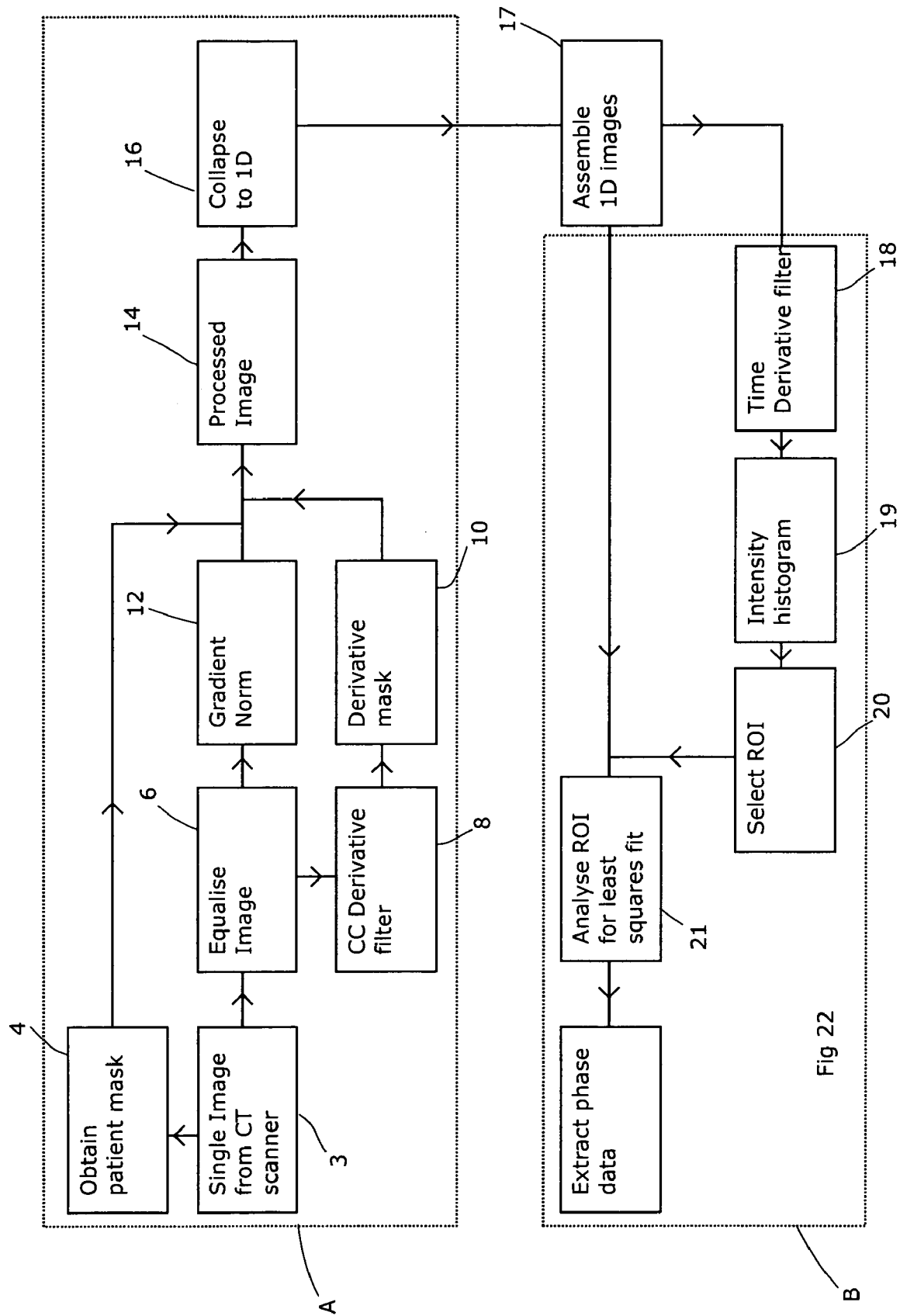
FIG. 22 shows, in outline, the process route applied to the images

The process according to the present invention will now be described. The general process route is set out in FIG. 22, on which the reference numerals employed correspond to the relevant earlier Figure of this application that illustrates the image or mask acquired at that point. Thus, after or during the acquisition of images from a cone beam CT or other similar scanner, a process route A is applied to each individual image 3. First, from the raw image 3, a patient mask 4 is obtained which is able to mask off the parts of the image that are external to the patient. To do so, a simple threshold can be set, and pixels or groups of pixels of the raw image 3 which have an intensity beyond that threshold can be allocated to the excluded area of the mask. In general, a trial and error process would be suitable to determine suitable patient mask depending on the parameters of the particular scanner being used, but in the case of the images used by the inventors a skin threshold of 20,000 was found to be suitable.

Again working from the raw image 3 obtained from the CT scanner, the image can then be equalised to reduce the contrast range. Many suitable equalisation filters are available, but in the present example the inventors adopted a scaled logarithmic approach in which the individual intensity values were converted to 1000 times the logarithm of the original intensity value.

From the equalised image, a derivative image is prepared, that is an image where the intensity values represent the rate of change of intensity in the pre-filtered image. A derivative filter must have an associated direction in which the rate of change is to be measured, and in the case of images of the thorax region of a patient it is preferred to use the craniocordal (CC) direction. This will then highlight changes in that direction. In a general case, the direction of this derivative should usually be aligned with the direction at step 16 below. From the derivative image, a derivative mask 10 can be provided, which is a mask highlighting those pixels where the derivative value is high. This therefore highlights the areas of the original equalised image where there is a rapid rate of change of intensity, i.e. areas of the equalised image 6 where there is an edge.

Finally, from the equalised image, a gradient norm image 12 is prepared. This is a form of equalised derivative image, in which the horizontal and vertical gradients are vector summed, i.e. the square of the horizontal gradient is added to the square of the vertical gradient and the square root of the result is taken.

The derivative mask 10 and the patient mask 4 can then be applied to the gradient norm image 12 to produce a processed image 14. This image will therefore contain the pixels of the equalised image that are both within the patient and in areas of a significant rate of change of intensity. In essence, this process selects out from the equalised image the edges within the patient, with a slight preference for CC-aligned edges. The preference is not complete, since although the CC edges are part of the mask, other edges are partly re-introduced in the form of the gradient norm. It should be noted that the algorithm is deliberately insensitive as to how the edges are extracted as attempts to identify the diaphragm usually fail. So long as the feature of interest (such as the diaphragm) is among the edges, the algorithm will detect one that moves significantly more than all other edges.

The last step in processing this image of the series of images produced by the scanner is to collapse the image down to one dimension, which in the case of a patient image should be aligned with the CC axis of the patient. This can be done by simply summing the total intensity along one horizontal row of pixels and adopting that intensity or an intensity derived therefrom as the intensity of the single pixel at that point along the horizontal axis. Thus, by this process each individual image from the scanner is reduced down to a simple linear image, one pixel wide by "n" pixels tall.

The process is then repeated for all or substantially all of the images in the series thereof derived from the scanner. This can be done as a post-processing step after acquisition of the entire series of images, or it can be commenced for the earlier edges while the later images are being enquired. Once the series of one-dimensional images are available, these can then be combined by juxtaposition to produce a composite image 17 in which, in essence, one axis corresponds to the CC axis of the patient (or the axis adopted for the one dimensional compression) whereas the other axis corresponds to a measure of time (as expressed by image number). The resultant image is shown in FIG. 17. Whilst it does not contain useful information about the entire structure of a patient, it does show useful information regarding the variation of the images with time. This information can be extracted by the series of processing steps B that are applied to the composite image.

Figure 18:
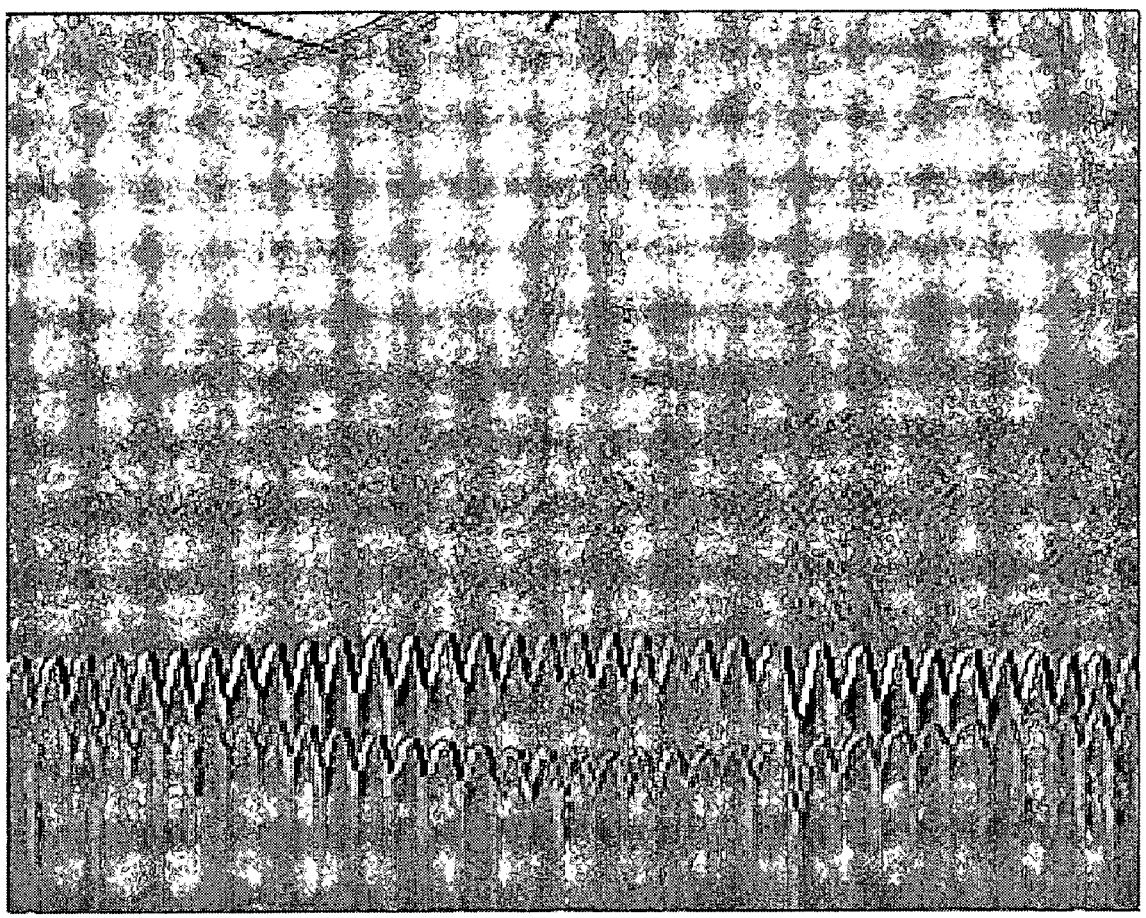
FIG. 18 shows the further image as filtered to highlight changes in the direction perpendicular to the one dimension.
Figure 19:
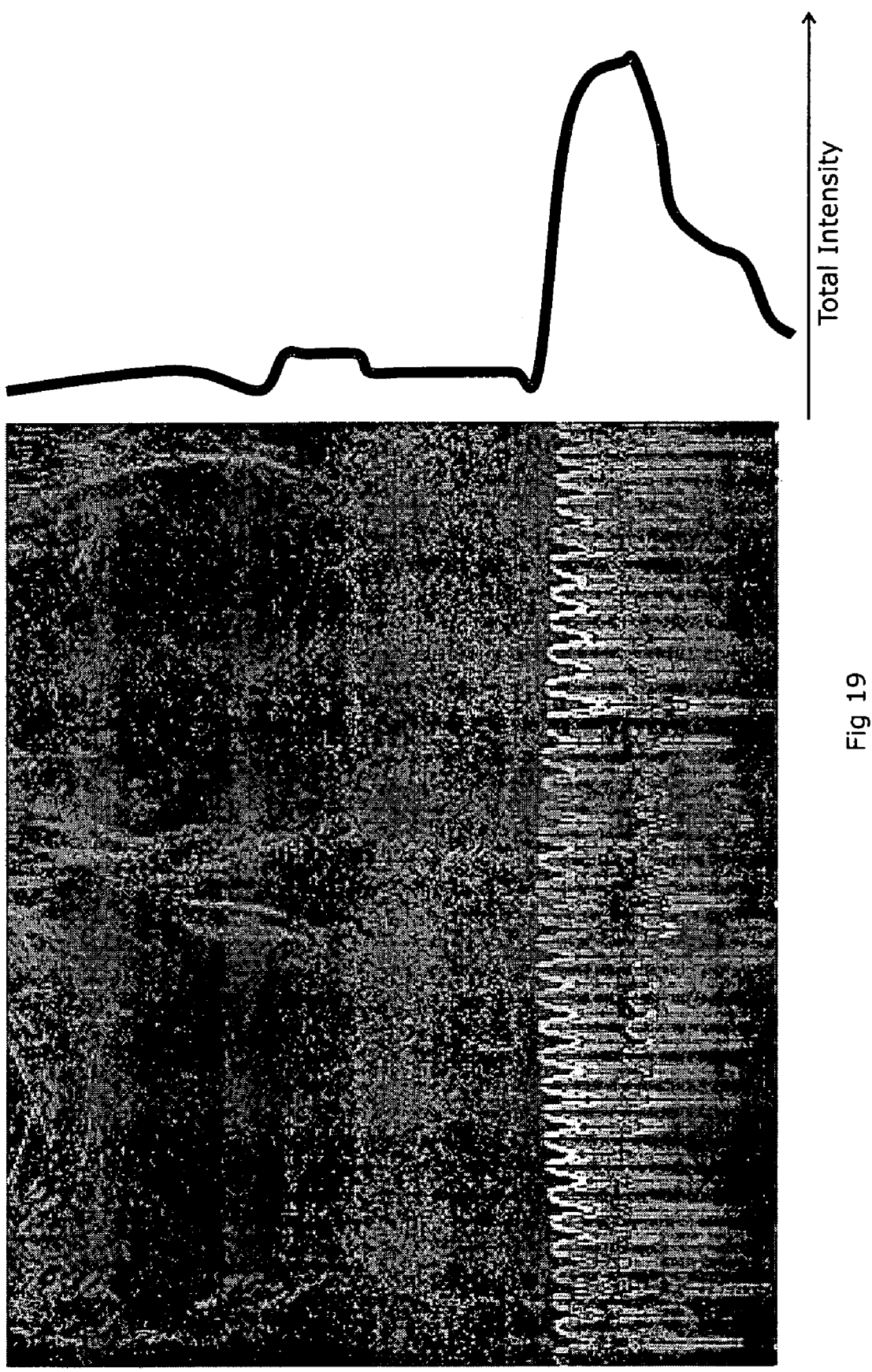
FIG. 19 shows the manner of selecting an area of interest in the further image.

First, a derivative filter is applied, with the derivative direction corresponding to the pixel number or time axis. This produces the image shown at FIG. 18 in which areas of rapid change with time are in effect highlighted.

The absolute value of the previous image (FIG. 18) is again mapped on the CC axis to form an intensity histogram. This one-dimensional signal highlights the position along the CC axis of the patient where there is maximum rate of change with image number or time. From the intensity histogram, a threshold can be applied to select a particular region of interest 20. Various thresholding methods are known and are suitable for this task, and include setting a simple fixed threshold, or a variable threshold that looks for the maxima and minima of the intensity histogram and adopts a threshold at a point therebetween. The region of interest can be limited to the precise area selected from the histogram, or there can be a margin either side.

Figure 20:
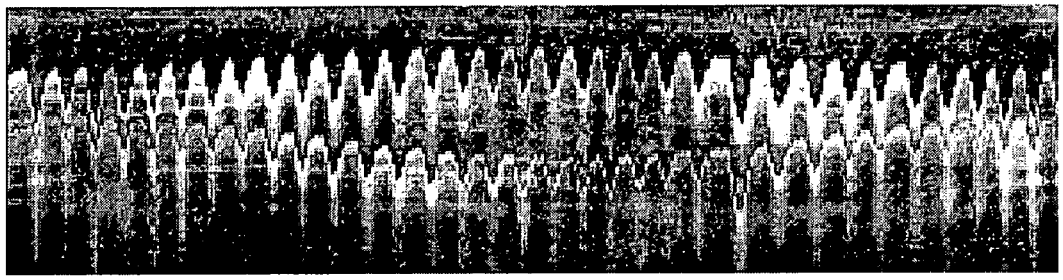
FIG. 20 shows the area of interest.

Having selected the region of interest, this area of the image 17 is then selected and analysed for periodic patterns. It can be seen in FIG. 20, the extracted region of interest, that there is a clear periodic pattern although this diverges into a pair of periodic patterns before reconverging by the end of the scan. This probably corresponds to the images of the left and right sides of the diaphragm of the patient concerned.

Figure 21:
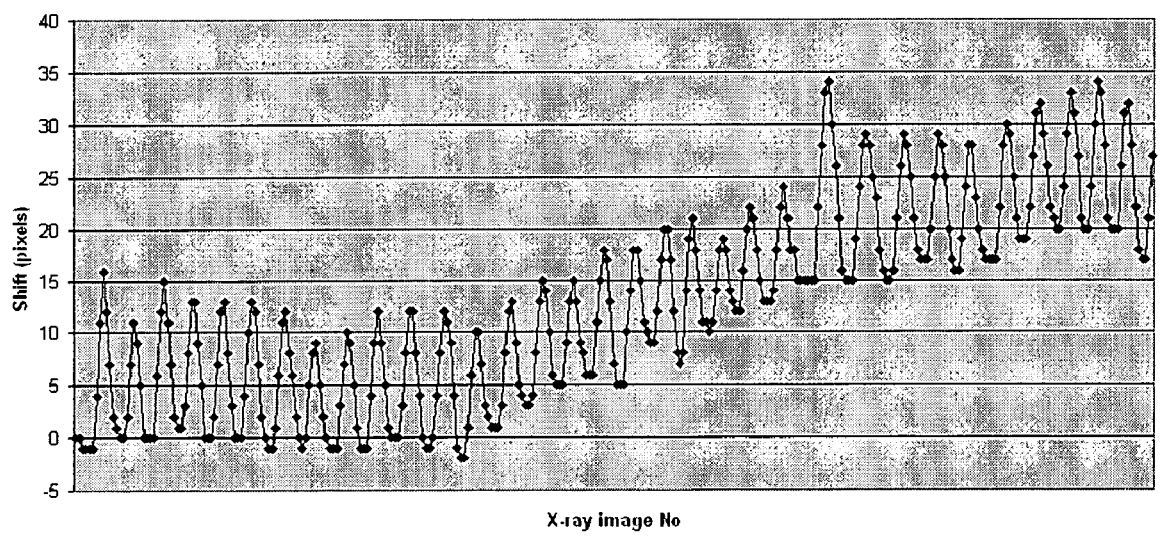
FIG. 21 shows the result of comparison of adjacent one-dimensional images.

To cope with this and other difficulties, an extremely simple comparison process is proposed in which each single-pixel "slice" of the image is compared to the next adjacent slice after being subjected to a variable shift. The system must then determine at what shift the difference is between the one-dimensional slices are minimised. One way of doing so, as shown in FIG. 21, is to sum the squares of the intensity differences between two single-pixel slices and to identify at what pixel shift that sum is at its minimum. After repeating that for each adjacent pair of one-pixel slices, the graph shown at FIG. 21 is derived at which the shift is shown varying with x-ray image number. This is a simple periodic graph which can be analysed using known techniques to determine its frequency and hence the phase position of each image.

Figure 23:
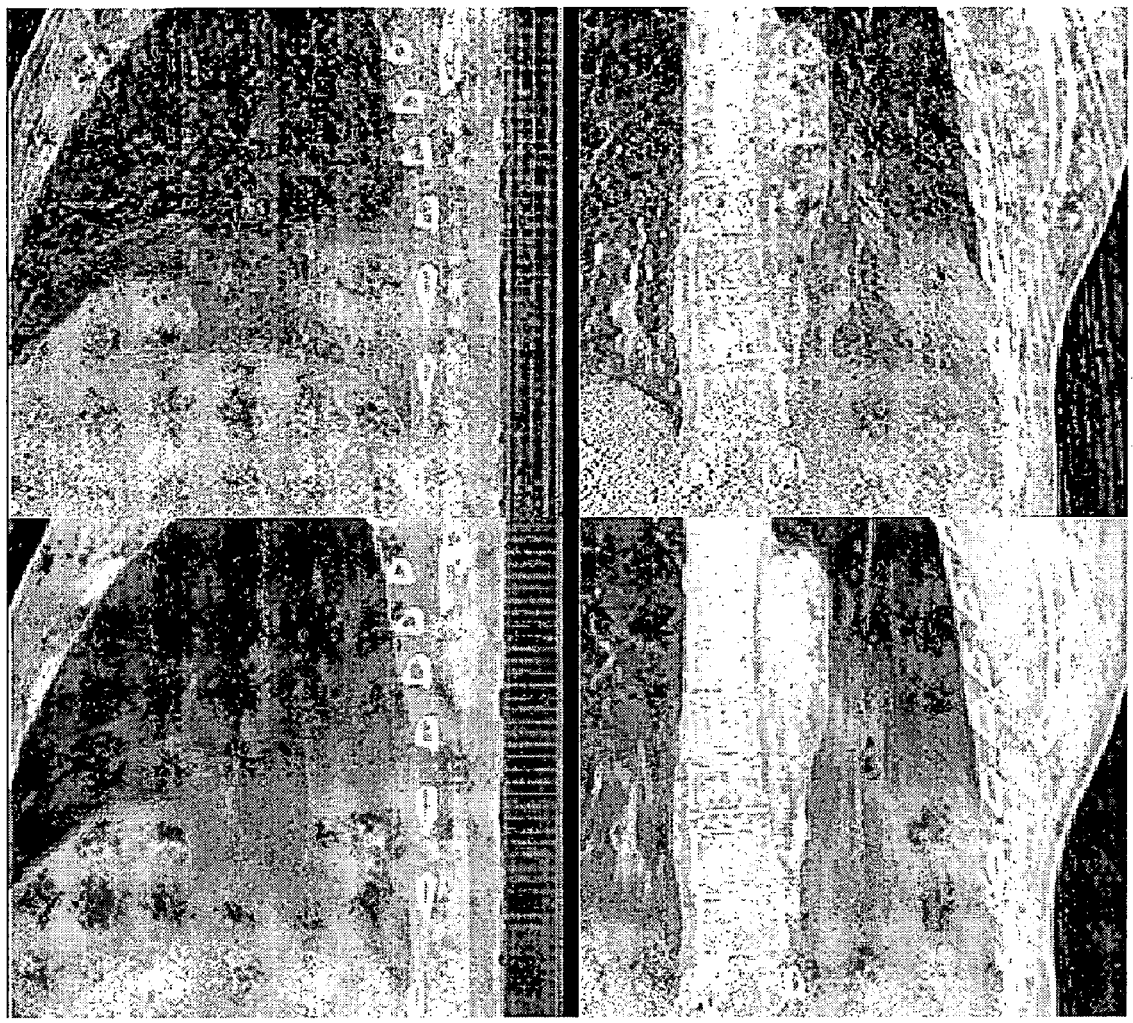
FIG. 23 shows the reconstructions obtained.

The system can then go back to each original image and assign phase information to it. The collected images can be organised into phase-correlated groups, and images within a single group can be used for a normal cone beam CT reconstruction process. The results are shown in FIG. 23 and illustrate a greater degree of precision and focus. Breathing artefacts are largely eliminated.

In experimental applications of this invention, the breathing cycles of four x-ray series derived from three patients were extracted. It was found that parameter values adopted to optimise the reconstruction in the first series proved to be appropriate for all. In particular, one of the three patients had only one lung, but insofar that breathing was visible in the x-ray images, the cycle was successfully extracted. Accordingly, the present invention provides a stand-alone algorithm for extracting the breathing cycle from sequential x-ray images which requires no user interaction and can, on a sufficiently fast processing engine, be used to produce good quality reconstructions within a usable time. Given that the crude initial values of the small number of parameters required for the algorithm prove to be appropriate for the entire tested series, the method is accordingly robust. Furthermore, the relative simplicity of the algorithm and the fact that much of the processing is on an image-by-image basis means that most of the processing can be done during the x-ray image acquisition time. On a suitably fast processor, processing of the composite image to reveal a breathing cycle frequency should not take more than about a second.

As the breathing cycle is derived directly from the x-ray images concerned, rather than from some secondary indication such as nasal temperature or chest size, there is less inaccuracy since the correlation between breathing cycle phase and x-ray image is direct.

It will of course be understood that many variations may be made to the above-described embodiment without departing from the scope of the present invention.

The invention claimed is:

1. Apparatus for imaging the internal structure of a volume exhibiting an internal variation, comprising:
   a source of penetrating radiation and a two dimensional detector for the radiation, the source and the detector being arranged to produce a series of projected images of the volume;
   a selection means for selecting images with similar phase from the series of projected images; and a reconstruction means for deriving information as to the three dimensional structure in the volume from the selected images;

wherein the selection means is arranged to:

collapse the images derived from the series from two dimensions to one dimension by summing the intensities of pixels along a dimension transverse to the one dimension, produce a further image from a composite of the one-dimensional images obtained from images in the series, analyze the further image for patterns, and select from the series images having like phase in that pattern.

2. Apparatus according to claim 1 in which the source and the detector are rotatable relative to the volume, such that the series of projected images show the volume in different orientations.

3. Apparatus according to claim 1 in which the variation is periodic.

4. Apparatus according to claim 1 in which the images are pre-processed prior to operation of the selection means.

5. Apparatus according to claim 4 in which the pre-processing includes filters for narrowing the range of intensities in the image.

6. Apparatus according to claim 4 in which the pre-processing includes derivative filters to highlight edges in the image.

7. Apparatus according to claim 6 in which the volume contains a patient and the derivative is carried out in the direction of a craniocordal axis of a patient.

8. Apparatus according claim 4 in which the pre-processing includes a mask applied to the image to select areas including edges.

9. Apparatus according to claim 8 in which the mask is derived from a threshold applied to the image as filtered via a derivative filter.

10. Apparatus according to claim 4 in which the pre-processing includes an application of a mask to exclude areas of the image that are external to an object within the volume.

11. Apparatus according to claim 1 in which a plurality of reconstructions are derived from a plurality of subsets each containing phase-correlated images from the series, the phase correlation of each subset differing from the phase correlation of other subsets.

12. Apparatus according to claim 1 in which the analysis for periodic patterns in the further image includes a step of comparison of the one-dimensional images therein to identify a movement of features in that dimension.

13. Apparatus according to claim 12 in which adjacent images are compared.

14. Apparatus according to claim 12 in which the one-dimensional images are compared by calculating the difference in intensity between the images at different relative shifts of the images.

15. Apparatus according to claim 14 in which the rms difference is compared.

16. Apparatus according to claim 1 in which the further image is subjected to processing prior to analysis for periodic patterns.

17. Apparatus according to claim 16 in which the pre-processing includes derivative filters to highlight edges in the further image.

18. Apparatus according to claim 17 in which the derivative is carried out in a direction transverse to the one dimension.

19. Apparatus according to claim 16 in which the pre-processing includes the selection of a region of interest in the further image and the exclusion of other areas from further processing.

20. Apparatus according to claim 19 in which the region of interest is selected by analysis of the area containing the highest derivatives.

21. Apparatus according to claim 1 in which the variation is a natural variation exhibited by living organism.

22. Apparatus according to claim 21 in which the variation is caused by breathing.

23. A method of selecting phase correlated images from the output of a scanner, comprising the steps of, for each of a plurality of images in a series thereof produced by the scanner:

collapsing the images from two dimensions to one dimension by summing the intensities of pixels along a dimension transverse to the one dimension, producing a further image from a composite of the one-dimensional images obtained from images in the series, analyzing the further image for periodic patterns, and selecting from the series images having like phase in that periodic pattern.

24. A method according to claim 23 in which the scanner is a cone beam CT scanner.

25. A method according to claim 24 in which the images are of a breathing patient.

26. A computer readable medium containing a computer program product for selecting phase correlated images from the output of a scanner, the computer program product comprising:

program code for executing the steps of, for each of a plurality of images in a series thereof produced by the scanner:

collapsing the images from two dimensions to one dimension by summing the intensities of pixels along a dimension transverse to the one dimension, producing a further image from a composite of the one-dimensional images obtained from images in the series, analyzing the further image for periodic patterns, and selecting from the series images having like phase in that periodic pattern.

27. A computer readable medium containing a computer program product according to claim 26 in which the scanner is a cone beam CT scanner.

28. A computer readable medium containing a computer program product according to claim 27 in which the images are of a breathing patient.

* * * * *